United States Patent [19]

Gruett et al.

[11] 4,305,948
[45] Dec. 15, 1981

[54] N-HYDROXY-1,2-DIHYDRO-2-OXO-5-(PYRIDINYL)-NICOTINIMIDAMIDE AND THEIR CARDIOTONIC USE

[75] Inventors: Monte D. Gruett; George Y. Lesher, both of Schodack, N.Y.

[73] Assignee: Sterling Drug Inc., New York, N.Y.

[21] Appl. No.: 218,616

[22] Filed: Dec. 22, 1980

[51] Int. Cl.$^3$ .................. A61K 31/44; C07D 401/04
[52] U.S. Cl. ..................................... 424/263; 546/257
[58] Field of Search ........................ 546/257; 424/263

[56] References Cited

U.S. PATENT DOCUMENTS 4,004,012  1/1977  Lesher et al. ..................... 424/263
4,072,746  2/1978  Lesher et al. ..................... 424/263

Primary Examiner—Richard Raymond
Attorney, Agent, or Firm—Robert K. Bair; B. Woodrow Wyatt

[57] ABSTRACT

N-Hydroxy-1-$R_1$-1,2-dihydro-2-oxo-5-PY-6-R-nicotinimidamides or pharmaceutically-acceptable acid-addition salts thereof, useful as cardiotonic agents, are prepared by reacting 1-$R_1$-1,2-dihydro-2-oxo-5-PY-6-R-nicotinonitriles with hydroxylamine and are converted by reaction with polyphosphoric acid to the corresponding cardiotonically useful 1-$R_1$-3-amino-5-PY-6-R-2(1H)-pyridinones, where $R_1$ is hydrogen, lower-alkyl and lower-hydroxyalkyl, R is hydrogen or lower-alkyl, and PY is 4- or 3-pyridinyl or 4- or 3-pyridinyl having one or two lower-alkyl substituents.

8 Claims, No Drawings

N-HYDROXY-1,2-DIHYDRO-2-OXO-5-(PYRIDINYL)-NICOTINIMIDAMIDE AND THEIR CARDIOTONIC USE

CROSS-REFERENCE TO RELATED APPLICATIONS

U.S. patent application Ser. No. 198,461, filed Oct. 20, 1980, discloses as cardiotonics and intermediates 1,2-dihydro-2-oxo-5-(pyridinyl)-6-(lower-alkyl)-nicotinonitriles, which are used herein as intermediates for preparing N-hydroxy-1,2-dihydro-2-oxo-5-(pyridinyl)-6-(lower-alkyl)nicotinimidamides.

The process aspects disclosed hereinbelow for preparing 3-amino-5-(pyridinyl)-2(1H)-pyridinones via the corresponding N-hydroxy-1,2-dihydro-2-oxo-5-(pyridinyl)-nicotinimidamide and for preparing said N-hydroxy-nicotinimidamide are disclosed and claimed in the copending divisional Application Ser. No. 262,187, filed on or about May 11, 1981.

BACKGROUND OF THE INVENTION (a) Field of the Invention

This invention relates to 1,2-dihydro-5-(pyridinyl)-2-oxonicotinamide derivatives, their preparation, their cardiotonic use and their conversion to the corresponding 3-amino-5-(pyridinyl)-2(1H)-pyridinones, also cardiotonics.

(b) Description of the Prior Art

Lesher and Opalka U.S. Pat. Nos. 4,004,012, issued Jan. 18, 1977, and 4,072,746, issued Feb. 7, 1978, show as cardiotonic agents 3-amino-5-(pyridinyl)-2(1H)-pyridinones and their preparation from the corresponding 3-carbamyl compounds. Said 3-carbamyl-5-(pyridinyl)-2(1H)-pyridinones, alternatively named 1,2-dihydro-2-oxo-5-(pyridinyl)nicotinamides, were shown only as intermediates.

SUMMARY OF THE INVENTION

In a composition of matter aspect, the invention resides in N-hydroxy-1-$R_1$-1,2-dihydro-2-oxo-5-PY-6-R-nicotinimidamide (I) or pharmaceutically-acceptable acid-addition salt thereof, where R, $R_1$ and PY are defined below.

A composition aspect of the invention resides in a cardiotonic composition for increasing cardiac contractility in a patient, said composition comprising a pharmaceutically-acceptable carrier and, as the active component thereof, a cardiotonically-effective amount of N-hydroxy-1-$R_1$-1,2-dihydro-2-oxo-5-PY-6-R-nicotinimidamide or pharmaceutically-acceptable acid-addition salt thereof.

In a method aspect, the invention resides in a method for increasing cardiac contractility in a patient requiring such treatment which comprises administering a medicament comprising a pharmaceutically-acceptable carrier and, as the active component thereof, a cardiotonically-effective amount of N-hydroxy-1-$R_1$-1,2-dihydro-2-oxo-5-PY-6-R-nicotinimamide or pharmaceutically-acceptable acid-addition salt thereof.

In a process aspect the invention comprises reacting 1-$R_1$-1,2-dihydro-2-oxo-5-PY-6-R-nicotinonitrile with hydroxylamine to produce N-hydroxy-1-$R_1$-1,2-dihydro-2-oxo-5-PY-6-R-nicotinimidamide (I) and reacting I with polyphosphoric acid to produce 1-$R_1$-3-amino-5-PY-6-R-2(1H)-pyridinone. Other process aspects comprise each of the above two steps, namely, the preparation of I and its conversion to 1-$R_1$-3-amino-5-PY-6-R-2(1H)-pyridinone.

DETAILED DESCRIPTION INCLUSIVE OF PREFERRED EMBODIMENTS

In a composition of matter aspect the invention resides in N-hydroxy-1-$R_1$-1,2-dihydro-2-oxo-5-PY-6-R-nicotinimidamide having formula I

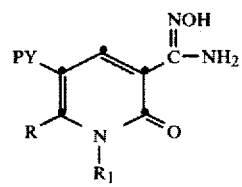

or pharmaceutically-acceptable acid-addition salt thereof, where R is hydrogen or lower-alkyl, $R_1$ is hydrogen, lower-alkyl or lower-hydroxyalkyl, and PY is 4- or 3-pyridinyl or 4- or 3-pyridinyl having one or two lower-alkyl substituents. The compounds of formula I are useful both as intermediates for preparing the corresponding cardiotonically useful 3-amino analogs of I and also as cardiotonic agents, as indicated by standard pharmacological evaluation procedures. Preferred embodiments are those of formula I where PY is 4- or 3-pyridinyl, $R_1$ is hydrogen and R is hydrogen, methyl or ethyl.

A composition aspect of the invention resides in a cardiotonic composition for increasing cardiac contractility, said composition comprising a pharmaceutically-acceptable carrier and, as the active component thereof, a cardiotonically-effective amount of N-hydroxy-1-$R_1$-1,2-dihydro-2-oxo-5-PY-6-R-nicotinimidamide or pharmaceutically-acceptable acid-addition salt thereof, where PY, R and $R_1$ have the meanings given above for the compounds of formula I. Preferred embodiments are those compositions where the active components are said preferred embodiments of formula I.

A method aspect of the invention resides in the method for increasing cardiac contractility in a patient requiring such treatment which comprises administering to such patient a composition comprising a pharmaceutically-acceptable carrier and, as the active component thereof, a cardiotonically-effective amount of N-hydroxy-1-$R_1$-1,2-dihydro-2-oxo-5-PY-6-R-nicotinimidamide (I) or pharmaceutically-acceptable acid-addition salt thereof, where PY, R and $R_1$ have the meanings given above for the compounds of formula I.

In a process aspect the invention comprises reacting 1-$R_1$-1,2-dihydro-2-oxo-5-PY-6-R-nicotinonitrile with hydroxylamine to produce N-hydroxy-1-$R_1$-1,2-dihydro-2-oxo-5-PY-6-R-nicotinimidamide (I) and reacting I with polyphosphoric acid to produce 1-$R_1$-3-amino-5-PY-6-R-2(1H)-pyridinone. Other process aspects comprise each of the above two steps, namely, the preparation of I and its conversion to 1-$R_1$-3-amino-5-PY-6-R-2(1H)-pyridinone. Preferred embodiments of the process aspects are those utilizing compounds where PY is 4- or 3-pyridinyl, $R_1$ is hydrogen and R is hydrogen, methyl or ethyl.

The term "lower-alkyl" as used herein, e.g., as one of the meanings of R or $R_1$ or as a substituent for PY in formula I, means an alkyl radical having from one to six carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

The term "lower-hydroxyalkyl", as used herein, e.g., as one of the meanings for $R_1$ in formula I, means a hydroxyalkyl radical having from two to six carbon atoms and having its hydroxy group and its free valence bond (or connecting linkage) on different carbon atoms, illustrated by 2-hydroxyethyl, 2-hydroxypropyl, 3-hydroxypropyl, 2-hydroxy-2-methylpropyl, 2-hydroxy-1,1-dimethylethyl, 4-hydroxybutyl, 5-hydroxypentyl, 6-hydroxyhexyl, and the like.

Illustrative of PY in formula I where PY is 4- or 3-pyridinyl having 1 or 2 lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The compounds of formula I are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to use the free base form; however, appropriate pharmaceutically-acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compound (I) are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound (I) are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structures of the compound of formula I were assigned on the basis of evidence provided by infrared, nuclear magnetic resonance and mass spectra, and by the correspondence of calculated and found values for the elemental analysis.

The manner of making and using the instant invention will now be generally described so as to enable a person skilled in the art of pharmaceutical chemistry to make and use the same, as follows.

The preparation of the intermediate 1-$R_1$-1,2-dihydro-2-oxo-5-PY-6-R-nicotinonitriles where R is lower-alkyl are described in the next three paragraphs. These intermediate nicotinonitriles are disclosed and claimed as cardiotonics in copending application Ser. No. 198,461 filed Oct. 20, 1980.

The preparation of 1-PY-2-(dimethylamino)ethenyl lower-alkyl ketone by reacting PY-methyl lower-alkyl ketone with dimethylformamide di-(lower-alkyl) acetal is carried out by mixing the reactants in the presence or absence of a suitable solvent. The reaction is conveniently run at room temperature, i.e., about 20°–25° C., or by warming the reactants up to about 100° C., preferably in an aprotic solvent, conveniently hexamethylphosphoramide because of the method used to prepare the PY-methyl lower-alkyl ketone, as noted below in Example A-1. Other suitable solvents include tetrahydrofuran, dimethylformamide, acetonitrile, ether, benzene, dioxane, and the like. Also, the reaction can be run without solvent, preferably using an excess of dimethylformamide di-(lower-alkyl)acetal. This procedure is further illustrated hereinbelow in Examples A-1 through A-11.

The intermediate PY-methyl lower-alkyl ketones are generally known compounds which are prepared by known methods [e.g., as given in Rec. trav. chim 72, 522 (1953); U.S. Pat. No. 3,133,077 (May 12, 1964); Bull. Soc. Chim 1968, 4132; Chem. Abstrs. 79, 8539h (1973); Chem. Abstrs. 81, 120,401a (1974); J. Org. Chem. 39, 3834 (1974); Chem. Abstrs. 87, 6594q (1977); J. Org. Chem. 43, 2286 (1978)].

The reaction of 1-PY-2-(dimethylamino)ethenyl lower-alkyl ketone with N-$R_1$-α-cyanoacetamide to produce 1-$R_1$-1,2-dihydro-2-oxo-5-PY-6-R-nicotinonitrile is carried out preferably by heating the reactants in a suitable solvent in the presence of a basic condensing agent. The reaction is conveniently run using an alkali lower-alkoxide, preferably sodium methoxide or ethoxide, in dimethylformamide. In practicing the invention, the reaction was carried out in refluxing dimethylformamide using sodium methoxide. Alternatively, methanol and sodium methoxide or ethanol and sodium ethoxide can be used as solvent and basic condensing agent, respectively; however, a longer heating period is required. Other basic condensing agents and solvents include sodium hydride, lithium diethylamide, lithium diisopropylamide, and the like, in an aprotic solvent, e.g., tetrahydrofuran, acetonitrile, ether, benzene, dioxane, and the like. This procedure is further illustrated hereinbelow in Examples B-1 through B-15.

The intermediate 1-$R_1$-1,2-dihydro-2-oxo-5-PY-6-R-nicotinonitriles where R is hydrogen are known, e.g., U.S. Pat. Nos. 4,004,012 and 4,072,746, noted hereinabove under Description of the Prior Art.

The reaction of 1-$R_1$-1,2-dihydro-2-oxo-5-PY-6-R-nicotinonitriles with hydroxylamine to produce N-hydroxy-1-$R_1$-1,2-dihydro-2-oxo-5-PY-6-R-nicotinimidamide by heating the reactants at about 50° C. to 100° C., preferably at about 60° C. to 65° C. and preferably in an appropriate solvent. The reaction was conveniently run in refluxing methanol.

The reaction of N-hydroxy-1-$R_1$-1,2-dihydro-2-oxo-5-PY-6-R-nicotinimidamide with polyphosphoric acid to produce 1-$R_1$-3-amino-5-PY-6-R-2(1H)-pyridinone was carried out by heating the reactants at about 50° C. to 100° C., preferably about 95° C. to 100° C.

The following examples will further illustrate the invention without, however, limiting it thereto.

A. 1-PY-2-(DIMETHYLAMINO)ETHENYL LOWER ALKYL KETONES

A-1. 1-(4-Pyridinyl)-2-(dimethylamino)ethenyl methyl ketone

A mixture containing 20 g. of (4-pyridinyl)-methyl methyl ketone [alternatively named 1-(4-pyridinyl)-2-propanone] and 30 cc. of hexamethylphosphoramide was diluted with 65 ml. of dimethylformamide dimethyl acetal and the resulting mixture was refluxed for 30 minutes. TLC analysis showed a single spot, thereby indicating completion of the reaction (in another run, the reaction appeared to be complete after 30 minutes at room temperature). The reaction mixture was evaporated under reduced pressure using a rotary evaporator and a pressure of about 15 mm., thereby resulting in a crystalline residue weighing 24 g. The residue was purified by continuous chromatographic extraction on alumina (about 150 g.) using chloroform (recycled by distillation onto the alumina) as eluant. After 1 and ½ hours, the extract was heated in vacuo to remove the chloroform, thereby leaving, as a light yellow crystalline material, 23.2 g. of 1-(4- pyridinyl)-2-(dimethylamino)ethenyl methyl ketone, alternatively named 4-dimethylamino-2-(4-pyridinyl)-3-buten-2-one.

The above preparation can be carried out using in place of hexamethylphosphoramide other solvents, e.g., dimethylformamide, acetonitrile or others noted above or in the absence of a solvent; however, hexamethylphosphoramide was conveniently used since (4-pyridinyl)methyl methyl ketone was conveniently prepared as a mixture together with hexamethylphosphoramide, as seen by the following preparation: To a stirred solution containing 70 ml. of freshly distilled diisopropylamine and 200 ml. of tetrahydrofuran at 0° C. under nitrogen was added dropwise over 20 minutes 210 cc. of 2.4 M n-butyllithium in n-hexane and the reaction mixture was stirred for about 35 minutes at about 0°-5° C. To the cold solution was added dropwise over a period of 10 minutes 90 ml. of dry hexamethylphosphoramide (no temperature change) and a resulting light yellow solution was stirred for 15 minutes. To the cold solution at 0° C. was added a solution of 50 ml. of 4-picoline in 150 ml. of dry tetrahydrofuran over a 15 minute period and stirring was continued for 30 minutes at 0° C. Next, a mixture containing 50 ml. of dry ethyl acetate and 150 ml. of tetrahydrofuran was added over a 15 minute period (temperature rose from 0° to about 6° C.) and the resulting mixture was stirred for 20 minutes at 0° C. The ice bath was then removed and stirring continued for another 90 minutes whereupon the temperature of the reaction mixture rose to about 25° C. The reaction mixture was then cooled in an ice bath and to it was added 60 ml. of acetic acid over a period of about 90 minutes. The tetrahydrofuran was distilled off using a rotary evaporator in vacuo. The remaining mixture was diluted with 400 ml. of water and the aqueous mixture was extracted successively with two 250 ml. portions of isopropyl acetate and three 80 ml. portions of chloroform. The solvents were distilled off under reduced pressure to yield about 137 g. of a mixture consisting primarily of the desired product and hexamethylphosphoramide. Another run using the same quantities was carried out as above except after the addition of 60 ml. of glacial acetic acid, the mixture was diluted with only 200 ml. of water, the phases were separated, and the aqueous phase was extracted with five 100 ml. portions of chloroform. The chloroform extract was washed with saline solution and the chloroform was distilled off in vacuo. The remaining mixture of the desired ketone and hexamethylphosphoramide was combined with the above 137 g. of the same mixture and the combined mixture was distilled under reduced pressure to yield the following fractions: I. 63 g., b.p. of 110°-112° C. at 4 mm.; II. 59 g. of pale yellow oil, b.p. 113°-115° C. at 3 mm.; and, III. 69 g. of pale yellow oil, b.p. 115°-118° C. at 2.5 mm. Examination of fraction III by NMR showed it to consist of a 2:3 mixture by weight of (4-pyridinyl)methyl methyl ketone and hexamethylphosphoramide.

Acid-addition salts of 1-(4-pyridinyl)-2-(dimethylamino)ethenyl methyl ketone are conveniently prepared by adding to a mixture of 5 g. of 1-(4-pyridinyl)-2-(dimethylamino)ethenyl methyl ketone in about 100 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1-(4-pyridinyl)-2-(dimethylamino)ethenyl methyl ketone and the appropriate acid, e.g., lactic acid or hydrochloric acid, to prepare respectively the monolactate or monohydrochloride salt in aqueous solution.

A-2. 1-(4-Pyridinyl)-2-(dimethylamino)ethenyl ethyl ketone

A mixture containing 87.5 g. of (4-pyridinyl)methyl ethyl ketone [alternatively named 1-(4-pyridinyl)-2-butanone] and 160 ml. of hexamethylphosphoramide was diluted with 100 g. of dimethylformamide dimethyl acetal and the resulting mixture was stirred under nitrogen at room temperature for 45 minutes. The methanol formed by the reaction was distilled off in vacuo using a rotary evaporator and the remaining material was distilled under reduced pressure to yield two fractions, one boiling at 45°-80° C. at 0.5 mm. and the second at 90°-95° C. at 0.5 mm. After TLC analysis showed predominantly a single spot for each fraction, the two fractions were combined (135 g.) and taken up in 600 ml. of chloroform. The resulting solution was washed with two 300 ml. portions of water and the water was back extracted with three 100 ml. portions of chloroform. The combined chloroform solution was dried over anhydrous sodium sulfate and purified by continuous extraction chromatography on 300 ml. of alumina using chloroform (recycled by distillation onto the alumina) as the eluant. The chloroform was distilled off in vacuo to yield a red oil which crystallized on standing overnight in an ice bath. The crystalline material was dissolved in carbon tetrachloride, cyclohexane was added and the mixture cooled to yield 64 g. of the resulting yellow crystalline product, 1-(4-pyridinyl)-2-(dimethylamino)ethenyl ethyl ketone. Another 11 g. of crystalline product was obtained from the mother liquor by continuous extraction chromatography on alumina using chloroform (recycled by distillation onto the alumina) as the eluant.

The above intermediate (4-pyridinyl)methyl ethyl ketone was obtained in a mixture with hexamethylphosphoramide as follows: To a mixture containing 200 ml. of tetrahydrofuran and 70 ml. of diisopropylamine under nitrogen at 0°–5° C. was added 210 ml. of 2.4 N n-butyllithium in n-hexane and the resulting mixture was stirred for 30 minutes. Next was added over a 10 minute period 90 ml. of hexamethylphosphoramide followed by stirring of the mixture for 15 minutes. Then was added over a 15 minute period a solution of 48 ml. of 4-picoline in 150 ml. of tetrahydrofuran followed by stirring for 30 minutes at about 0° C. The ice/acetone bath cooling the reaction mixture was replaced with a dry ice/acetone bath and to the reaction mixture was added over a 20 minute period a mixture of 75 ml. of ethyl propionate in an equal volume of tetrahydrofuran. The reaction mixture was then allowed to warm up to room temperature over a period of about 90 minutes and then was warmed at about 35° C. for 30 minutes. The mixture was next cooled in an ice/acetone bath and to it was added 60 ml. of glacial acetic acid over 30 minutes. The resulting pale yellow suspension was diluted with 200 ml. of water. The mixture was extracted with three 150 ml. portions of ethyl acetate and the ethyl acetate extract was back washed with saline solution. The extract was heated in vacuo to remove the ethyl acetate and the residue was taken up again with ethyl acetate. The solution was washed with water and then heated in vacuo to remove the ethyl acetate followed by heating the residue in vacuo at 50° C. for about 30 minutes to yield 100 g. of pale yellow oil. The pale yellow oil was combined with corresponding samples obtained from two additional runs and then distilled in vacuo to yield a 256 g. fraction, b.p. 85°–105° C. at 0.5–1.0 mm. The NMR of this fraction showed it to be a mixture of (4-pyridinyl)methyl ethyl ketone and hexamethylphosphoramide in a respective molar ratio of 1:1.55, that is, 35% or 0.35×256=90 g. of said ketone.

A-3. 1-(4-Pyridinyl)-2-(dimethylamino)ethenyl n-propyl ketone

A mixture containing 80 g. of (4-pyridinyl)methyl n-propyl ketone [alternatively named 1-(4-pyridinyl)-2-pentanone] and 46 cc. of hexamethylphosphoramide was diluted with 250 ml. of acetonitrile. To the mixture was added 90 ml. of dimethylformamide dimethyl acetal and the resulting reaction mixture was heated on a steam bath for ninety minutes and then distilled under vacuum at about 2 mm. to remove volatile materials, including methanol, acetonitrile and hexamethylphosphoramide. The remaining residue was diluted with ethyl acetate and washed with water. The combined water washings were extracted with five 150 cc. portions of ethyl acetate. The combined ethyl acetate solutions were washed with saline solution, dried over anhydrous sodium sulfate, filtered and evaporated to dryness. The residue crystallized while standing in a freezer. The crystalline product was slurried with cyclohexane, filtered and dried overnight at 30° C. to produce, as a yellow crystalline product, 97 g. of 1-(4-pyridinyl)-2-(dimethylamino)ethenyl n-propyl ketone, m.p. 48°–50° C.

The above intermediate (4-pyridinyl)methyl n-propyl ketone was obtained in a mixture with hexamethylphosphoramide as follows: To a stirred solution of 70 ml. of diisopropylamine in 200 ml. of tetrahydrofuran under nitrogen at about 0° C. (use of ice bath) was added 210 cc. of 2.4 N n-butyllithium over twenty minutes and the resulting mixture was stirred for 30 minutes at about 0° C. to the mixture was added with stirring over ten minutes 90 ml. of hexamethylphosphoramide and the resulting mixture was stirred for another ten minutes. Next 45 ml. of 4-picoline in 140 ml. of tetrahydrofuran was added dropwise over fifteen to twenty minutes. The resulting dark orange-brown solution was stirred at 0° C. for thirty minutes and then treated dropwise over an eighteen minute period a solution consisting of 68 ml. of ethyl butyrate in 68 ml. of tetrahydrofuran, the temperature rising from −8° C. to +8° to 10° C. The reaction mixture was removed from the ice bath and allowed to warm up to room temperature for over seventy-five minutes. The reaction mixture was recooled and to it was added dropwise over fifteen minutes 60 ml. of glacial acetic acid. A pale yellow solid separated, resulting in a suspension. The suspension was diluted with water and extracted with two 200 ml. portions of ethyl acetate. The ethyl acetate extract was washed with three 100 ml. portions of saline solution, dried over anhydrous sodium sulfate and evaporated in vacuo to yield 107 g. of a mixture consisting primarily of (4-pyridinyl)methyl n-propyl ketone and hexamethylphosphoramide. The mixture obtained in this run was combined with corresponding mixtures obtained in two other runs and the combined mixtures were distilled under vacuum to produce, as the major fraction, b.p. 80°–90° C. at 0.2 mm., a mixture consisting of 80 g. of (4-pyridinyl)methyl n-propyl ketone and 46 g. of hexamethylphosphoramide.

Following the procedure described in Example A-2 but using a molar equivalent quantity of the appropriate PY-methyl lower-alkyl ketone in place of (4-pyridinyl)-methyl ethyl ketone, it is contemplated that the corresponding 1-PY-2-(dimethylamino)ethenyl lower-alkyl ketones of Examples A-4 thru A-11 can be obtained.

A-4. 1-(3-Pyridinyl)-2-(dimethylamino)ethenyl methyl ketone using (3-pyridinyl)methyl methyl ketone.

A-5. 1-(4-Pyridinyl)-2-(dimethylamino)ethenyl isopropyl ketone using (4-pyridinyl)methyl isopropyl ketone.

A-6. 1-(4-Pyridinyl)-2-(dimethylamino)ethenyl n-butyl ketone using (4-pyridinyl)methyl n-butyl ketone.

A-7. 1-(4-Pyridinyl)-2-(dimethylamino)ethenyl isobutyl ketone using (4-pyridinyl)methyl isobutyl ketone.

A-8. 1-(4-Pyridinyl)-2-(dimethylamino)ethenyl tert-butyl ketone using (4-pyridinyl)methyl tert.-butyl ketone.

A-9. 1-(4-Pyridinyl)-2-(dimethylamino)ethenyl n-pentyl ketone using (4-pyridinyl)methyl n-pentyl ketone.

A-10. 1-(2-Methyl-4-pyridinyl)-2-(dimethylamino)-ethenyl ethyl ketone using (2-methyl-4-pyridinyl)-methyl ethyl ketone.

A-11. 1-(3-Pyridinyl)-2-(dimethylamino)ethenyl ethyl ketone using (3-pyridinyl)methyl ethyl ketone.

B.
1-R₁-1,2-DIHYDRO-6-(LOWER-ALKYL)-2-OXO-5-PY-NICOTINO-NITRILES

B-1.
1,2-Dihydro-6-methyl-2-oxo-5-(4-pyridinyl)nicotinonitrile, alternatively named 1,6-dihydro-2-methyl-6-oxo-[3,4'-bipyridine]-5-carbonitrile To a mixture containing 23 g. of 1-(4-pyridinyl)-2-(dimethylamino)ethenyl methyl ketone and 11 g. of α-cyanoacetamide dissolved in 400 ml. of dimethylformamide was added with stirring 14 g. of sodium methoxide and the resulting reaction mixture was heated in an oil bath under gentle reflux for one hour. TLC analysis showed no starting material in the reaction mixture which was then concentrated in vacuo on a rotary evaporator to a volume of about 80 ml. The concentrate was treated with about 160 ml. of acetonitrile and the resulting mixture was stirred on a rotary evaporator with warming until homogenuous and then cooled. The crystalline product was collected, rinsed successively with acetonitrile and ether, and dried overnight at 55° C. to yield 28 g. of tan crystalline product, namely, sodium salt of 1,2-dihydro-6-methyl-2-oxo-5-(4-pyridinyl)nicotinonitrile, the presence of cyano being confirmed by IR analysis. An 8 g. portion of said sodium salt was dissolved in 75 ml. of hot water, the aqueous solution treated with decolorizing charcoal filtered, the filtrate again treated with decolorizing charcoal and filtered, and the filtrate acidified with 6 N-hydrochloric acid by dropwise addition to a pH of 3. The acidic mixture was diluted with ethanol and cooled. The crystalline product was collected, dried, recrystallized from dimethylformamide-water and dried to produce 3.75 g. of 1,2-dihydro-6-methyl-2-oxo-5-(4-pyridinyl)-nicotinonitrile, m.p., >300° C.

Acid-addition salts of 1,2-dihydro-6-methyl-2-oxo-5-(4-pyridinyl)nicotinonitrile are conveniently prepared by adding to a mixture of 2 g. of 1,2-dihydro-6-methyl-2-oxo-5-(4-pyridinyl)nicotinonitrile in about 40 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 1,2-dihydro-6-methyl-2-oxo-5-(4-pyridinyl)nicotinonitrile and the appropriate acid, e.g., lactic acid or hydrochloric acid, to prepare respectively the monolactate or monohydrochloride salt in aqueous solution.

B-2.
6-Ethyl-1,2-dihydro-2-oxo-5-(4-pyridinyl)-nicotinonitrile, alternatively named 2-ethyl-1,6-dihydro-6-oxo-[3,4'-bipyridine]-5-carbonitrile, m.p. 300° C., 11.6 g., was prepared following the procedure described above in Example B-1 using 20 g. of 1-(4-pyridinyl)-2-(dimethylamino)ethenyl ethyl ketone, 8.4 g. of α-cyanoacetamide, 16.2 g. of sodium methoxide and 250 ml. of dimethylacetamide (as solvent in place of dimethylformamide).

B-3.
1,2-Dihydro-2-oxo-6-n-propyl-5-(4-pyridinyl)-nicotinonitrile, alternatively named 1,6-dihydro-6-oxo-2-n-propyl-[3,4'-bipyridine]-5-carbonitrile, m.p. 232°-234° C., 9.9 g., was prepared following the procedure described above in Example B-1 using 85 g. of 1-(4-pyridinyl)-2-(dimethylamino)ethenyl n-propyl ketone, 36.5 g. of α-cyanoacetamide, 50 g. of sodium methoxide and 800 ml. of dimethylacetamide.

B-4.
1,2-Dihydro-1,6-dimethyl-2-oxo-5-(4-pyridinyl)-nicotinonitrile, alternatively named 1,6-dihydro-1,2-dimethyl-6-oxo-(3,4'-bipyridine)-5-carbonitrile, m.p. 245°-248° C., 32.3 g., was prepared following the procedure described above in Example B-1 using 42.5 g. of 1-(4-pyridinyl)-2-(dimethylamino)ethenyl methyl ketone, 23.5 g. of N-methyl-α-cyanoacetamide, 6.7 g. of sodium methoxide, 400 ml. of methanol and a refluxing period of two hours.

Following the procedure described in Example B-2 but using a molar equivalent quantity of the appropriate 1-PY-2-(dimethylamino)ethenyl lower-alkyl ketone in place of 1-(4-pyridinyl)-2-(dimethylamino)ethenyl ethyl ketone and the appropriate N-R₁-α-cyanoacetamide, it is contemplated that the corresponding 1-R₁-1,2-dihydro-2-oxo-5-PY-6-R-nicotinonitriles of Examples B-5 thru B-15 can be obtained.

B-5.
1,2-Dihydro-6-methyl-2-oxo-5-(3-pyridinyl)-nicotinonitrile, using 1-(3-pyridinyl)-2-(dimethylamino)ethenyl methyl ketone and α-cyanoacetamide.

B-6.
1,2-Dihydro-6-isopropyl-2-oxo-5-(4-pyridinyl)-nicotinonitrile, using 1-(4-pyridinyl)-2-(dimethylamino)ethenyl isopropyl ketone and α-cyanoacetamide.

B-7.
6-n-Butyl-1,2-dihydro-2-oxo-5-(4-pyridinyl)-nicotinonitrile, using 1-(4-pyridinyl)-2-(dimethylamino)ethenyl n-butyl ketone and α-cyanoacetamide.

B-8.
1,2-Dihydro-6-isobutyl-2-oxo-5-(4-pyridinyl)-nicotinonitrile, using 1-(4-pyridinyl)-2-(dimethylamino)ethenyl isobutyl ketone and α-cyanoacetamide.

B-9.
1,2-Dihydro-2-oxo-5-(4-pyridinyl)-6-tert.-butyl-nicotinonitrile, using 1-(4-pyridinyl)-2-(dimethylamino)ethenyl tert.-butyl ketone and α-cyanoacetamide.

B-10.
1,2-Dihydro-2-oxo-6-n-pentyl-5-(4-pyridinyl)-nicotinonitrile, using 1-(4-pyridinyl)-2-(dimethylamino)ethenyl n-pentyl ketone and α-cyanoacetamide.

B-11.
6-Ethyl-1,2-dihydro-5-(2-methyl-4-pyridinyl)-2-oxonicotinonitrile, using 1-(2-methyl-4-pyridinyl)-2-(dimethylamino)ethenyl ethyl ketone and α-cyanoacetamide.

B-12.
6-Ethyl-1,2-dihydro-2-oxo-5-(3-pyridinyl)-nicotinonitrile, using 1-(3-pyridinyl)-2-(dimethylamino)ethenyl ethyl ketone and α-cyanoacetamide.

B-13.
6-Ethyl-1,2-dihydro-1-(2-hydroxyethyl)-2-oxo-5-(4-pyridinyl)nicotinonitrile, using 1-(4-pyridinyl)-2-(dimethylamino)ethenyl ethyl ketone and N-(2-hydroxyethyl)-α-cyanoacetamide.

B-14.
1-Ethyl-1,2-dihydro-6-methyl-2-oxo-5-(4-pyridinyl)nicotinonitrile, using 1-(4-pyridinyl)-2-dimethylamino)ethenyl methyl ketone and N-ethyl-α-cyanoacetamide.

B-15.
1,6-Diethyl-1,2-dihydro-2-oxo-5-(4-pyridinyl)-nicotinonitrile, using 1-(4-pyridinyl)-2-(dimethylamino)ethenyl ethyl ketone and N-ethyl-α-cyanoacetamide.

C. N-HYDROXY-1-R₁-1,2-DIHYDRO-2-OXO-5-PY-6-R-NICOTINIMIDAMIDES

C-1. N-HYDROXY-1,2-DIHYDRO-2-OXO-5-(4-PYRIDINYL)NICOTINIMIDAMIDE, alternatively named N-hydroxy-1,6-dihydro-6-oxo-[3,4'-bipyridin]-5-carboximidamide To a solution containing 8.0 g. of sodium hydroxide dissolved in 500 ml. of absolute methanol was added with stirring 15.9 g. of hydroxylamine hydrochloride. To the resulting stirred mixture containing precipitated sodium chloride was added 19.7 g. of 1,2-dihydro-2-oxo-5-(4-pyridinyl)nicotinonitrile and the resulting suspension was refluxed with stirring on a steam bath for forty-three hours. The resulting bright yellow solid that separated was collected, washed with a small quantity of fresh methanol and was then triturated twice with water to remove sodium chloride. The remaining product was dried in a vacuum oven at 90° C. to yield 20.6 g. of N-hydroxy-1,2-dihydro-2-oxo-5-(4-pyridinyl)nicotinimidamide m.p. 228° C. with decomposition.

Acid-addition salts of N-hydroxy-1,2-dihydro-2-oxo-5-(4-pyridinyl)nicotinimidamide are conveniently prepared by adding to a mixture of 2 g. of N-hydroxy-1,2-dihydro-2-oxo-5-(4-pyridinyl)nicotinimidamide in about 40 ml. of aqueous methanol the appropriate acid, e.g., methanesulfonic acid, concentrated sulphuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of N-hydroxy-1,2-dihydro-2-oxo-5-(4-pyridinyl)nicotinimidamide and the appropriate acid, e.g., lactic acid or hydrochloric acid, to prepare respectively the monolactate or monohydrochloride salt in aqueous solution.

Following the procedure described in Example C-1 but using a molar equivalent quantity of the appropriate 1-R₁-1,2-dihydro-2-oxo-5-PY-6-R-nicotinonitrile in place of 1,2-dihydro-2-oxo-5-(4-pyridinyl)nicotinonitrile, it is contemplated that the corresponding N-hydroxy-1-R₁-1,2-dihydro-2-oxo-5-PY-6-R-nicotinimidamides of Examples C-2 thru C-13 can be obtained.

C-2. N-Hydroxy-1,2-dihydro-6-methyl-2-oxo-5-(3-pyridinyl)nicotinimidamide, using 1,2-dihydro-6-methyl-2-oxo-5-(3-pyridinyl)nicotinonitrile.

C-3. N-Hydroxy-1,2-dihydro-6-isopropyl-2-oxo-5-(4-pyridinyl)nicotinimidamide, using 1,2-dihydro-6-isopropyl-2-oxo-5-(4-pyridinyl)nicotinonitrile.

C-4. N-6-n-butyl-1,2-dihydro-2-oxo-5-(4-pyridinyl)nicotinimidamide, using 6-n-butyl-1,2-dihydro-2-oxo-5-(4-pyridinyl)nicotinonitrile.

C-5. N-Hydroxy-1,2-dihydro-6-isobutyl-2-oxo-5-(4-pyridinyl)nicotinimidamide, using 1,2-dihydro-6-isobutyl-2-oxo-5-(4-pyridinyl)nicotinonitrile.

C-6. N-Hydroxy-1,2-dihydro-2-oxo-5-(4-pyridinyl)-6-tert.-butylnicotinimidamide, using 1,2-dihydro-2-oxo-5-(4-pyridinyl)-6-tert.-butylnicotinonitrile.

C-7. N-Hydroxy-1,2-dihydro-2-oxo-6-n-pentyl-5-(4-pyridinyl)nicotinimidamide, using 1,2-dihydro-2-oxo-6-n-pentyl-5-(4-pyridinyl)nicotinonitrile.

C-8. N-Hydroxy-6-ethyl-1,2-dihydro-5-(2-methyl-4-pyridinyl)-2-oxonicotinimidamide, using 6-ethyl-1,2-dihydro-5-(2-methyl-4-pyridinyl)-2-oxonicotinonitrile.

C-9. N-Hydroxy-6-ethyl-1,2-dihydro-2-oxo-5-(3-pyridinyl)nicotinimidamide, using 6-ethyl-1,2-dihydro-2-oxo-5-(3-pyridinyl)nicotinonitrile.

C-10. N-Hydroxy-6-ethyl-1,2-dihydro-1-(2-hydroxyethyl)-2-oxo-5-(4-pyridinyl)nicotinimidamide, using 6-ethyl-1,2-dihydro-1-(2-hydroxyethyl)-2-oxo-5-(4-pyridinyl)nicotinonitrile.

C-11. N-Hydroxy-1,2-dihydro-6-methyl-2-oxo-5-(4-pyridinyl)nicotinimidamide, using 1,2-dihydro-6-methyl-2-oxo-5-(4-pyridinyl)nicotinonitrile.

C-12. N-Hydroxy-1-ethyl-1,2-dihydro-6-methyl-2-oxo-5-(4-pyridinyl)nicotinimidamide, using 1-ethyl-1,2-dihydro-6-methyl-2-oxo-5-(4-pyridinyl)nicotinonitrile.

C-13. N-Hydroxy-1,6-diethyl-1,2-dihydro-2-oxo-5-(4-pyridinyl)nicotinimidamide, using 1,6-diethyl-1,2-dihydro-2-oxo-5-(4-pyridinyl)nicotinonitrile.

D. 1-R₁-3-AMINO-5-PY-6-R-2(1H)-PYRIDINONES

D-1. 3-Amino-5-(4-pyridinyl)-2(1H)pyridinone

A mixture containing 2.0 g. of N-hydroxy-1,2-dihydro-2-oxo-5-(4-pyridinyl)nicotinimidamide and 16 g. of polyphosphoric acid was stirred with a glass rod until a stiff paste was obtained. The mixture was then heated on a steam bath with occasional stirring for 12 hours and then allowed to stand at room temperature over the weekend. The reaction mixture was warmed a little to soften the viscous mixture which was then treated with about 100 ml. of water and mixed well to dissolve the excess polyphosphoric acid. A yellow solid material that separated was collected, suspended in fresh water and to the suspension was added ammonium hydroxide until the mixture was distinctly alkaline. The solid which did not dissolve was collected, washed with a little water and dried in a vacuum oven at 90° C. to produce 0.9 g. of 3-amino-5-(4-pyridinyl)-2(1H)pyridinone, m.p. 293°-295° C. with decomposition. This product was identical with a sample of amrinone, that is, 3-amino-5-(4-pyridinyl)-2(1H)pyridinone which had been prepared from its corresponding 3-carbamyl precursor as shown in U.S. Pat. No. 4,072,746.

Following the procedure described in Example D-1 but using a molar equivalent quantity of the appropriate N-hydroxy-1-R₁-1,2-dihydro-2-oxo-5-PY-6-R-nicotinimidamide in place of N-hydroxy-1,2-dihydro-2-oxo-5-(4-pyridinyl)nicotinimidamide, it is contemplated that the corresponding 1-R₁-3-amino-PY-6-R-2(1H)-pyridinones of Examples D-2 thru D-12 can be obtained.

D-2. 3-Amino-6-methyl-5-(3-pyridinyl)-2(1H)pyridinone, using N-hydroxy-1,2-dihydro-6-methyl-2-oxo-5-(3-pyridinyl)nicotinimidamide.

D-3. 3-Amino-6-isopropyl-5-(4-pyridinyl)-2(1H)pyridinone, using N-hydroxy-1,2-dihydro-6-isopropyl-2-oxo-5-(4-pyridinyl)nicotinimidamide.

D-4. 3-Amino-6-n-butyl-5-(4-pyridinyl)-2(1H)pyridinone, using N-hydroxy-6-n-butyl-1,2-dihydro-2-oxo-5-(4-pyridinyl)nicotinimidamide.

D-5. 3-Amino-6-isobutyl-5-(4-pyridinyl)-2(1H)pyridinone, using N-hydroxy-1,2-dihydro-6-isobutyl-2-oxo-5-(4-pyridinyl)nicotinimidamide.

D-6. 3-Amino-5-(4-pyridinyl)-6-tert.-butyl-2(1H)pyridinone, using N-hydroxy-1,2-dihydro-2-oxo-5-(4-pyridinyl)-6-tert.-butylnicotinimidamide.

D-7. 3-Amino-6-n-pentyl-5-(4-pyridinyl)-2(1H)pyridinone, using N-hydroxy-1,2-dihydro-2-oxo-6-n-pentyl-5-(4-pyridinyl)nicotinimidamide.

D-8. 3-Amino-6-ethyl-5-(2-methyl-4-pyridinyl)-2(1H)pyridinone, using N-hydroxy-6-ethyl-1,2-dihydro-5-(2-methyl-4-pyridinyl)-2-oxonicotinimidamide.

D-9. 3-Amino-6-ethyl-5-(3-pyridinyl)-2(1H)pyridinone, using N-hydroxy-6-ethyl-1,2-dihydro-2-oxo-5-(3-pyridinyl)nicotinimidamide.

D-10. 3-Amino-6-ethyl-1-(2-hydroxyethyl)-5-(4-pyridinyl)-2(1H)pyridinone, using N-hydroxy-6-ethyl-1,2-dihydro-1-(2-hydroxyethyl)-2-oxo-5-(4-pyridinyl)nicotinimidamide.

D-11. 3-Amino-1-ethyl-6-methyl-5-(4-pyridinyl)-2(1H)pyridinone, using N-hydroxy-1-ethyl-1,2-dihydro-6-methyl-2-oxo-5-(4-pyridinyl)nicotinimidamide.

D-12. 3-Amino-1,6-diethyl-5-(4-pyridinyl)-2(1H)pyridinone, using N-hydroxy-1,6-diethyl-1,2-dihydro-2-oxo-5-(4-pyridinyl)nicotinimidamide.

The usefulness of the compounds of formula I or salts thereof as cardiotonic agents is demonstrated by their effectiveness in standard pharmacological test procedures, for example, in causing a significant increase in contractile force in the Isolated Cat Atria and Papillary Muscle Procedure and in causing a significant increase in cardiac contractile force in the Anesthetized Dog Procedure with low or minimal changes in heart rate and blood pressure. Detailed descriptions of these test procedures appear in U.S. Pat. No. 4,072,746, issued Feb. 7, 1980.

When tested by the above-noted Isolated Cat Atria and Papillary Muscle Procedure, the compounds of formula I when tested at doses of 100 or 300 μg./ml., were found to cause a significant increase, that is, greater than 25%, in papillary muscle force and a significant increase, that is, greater than 25%, in right atrial force, while causing a lower percentage increase (about one-half or less than the percentage increase in right atrial force or papillary muscle force) in right atrial rate; for example, N-hydroxy-1,2-dihydro-2-oxo-5-(4-pyridinyl)nicotinimidamide (Example C-1), when tested by said procedure was found to cause a 25% increase in each of papillary muscle force and right atrial force at 100 μg/ml and 48% and 43% increases respectively in papillary muscle force and right atrial force at 300 μg/ml.

The present invention includes within its scope a cardiotonic composition for increasing cardiac contractility, said composition comprising a pharmaceutically-acceptable carrier and, as the active component thereof, a cardiotonically-effective amount of N-hydroxy-1-R₁-1,2-dihydro-2-oxo-5-PY-6-R-nicotinimidamide of formula I or pharmaceutically-acceptable acid-addition or cationic salt thereof. The invention also includes within its scope the method for increasing cardiac contractility in a patient requiring such treatment which comprises administering to such patient a composition comprising a pharmaceutically-acceptable carrier and, as the active component thereof, a cardiotonically-effective amount of said N-hydroxy-1-R₁-1,2-dihydro-2-oxo-5-PY-6-R-nicotinimidamide (I) or pharmaceutically-acceptable acid-addition or cationic salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavouring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentages of active components in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. N-Hydroxy-1-R₁-1,2-dihydro-2-oxo-5-PY-6-R-nicotinimidamide having the formula

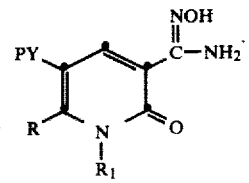

or pharmaceutically-acceptable acid-addition salt thereof, where R is hydrogen or lower-alkyl, R₁ is hydrogen, lower-alkyl or lower-hydroxyalkyl, and PY is 4- or 3-pyridinyl or 4- or 3-pyridinyl having one or two lower-alkyl substituents.

2. A compound according to claim 1 where PY is 4- or 3-pyridinyl.

3. A compound according to claim 1 where $R_1$ is hydrogen and R is hydrogen, methyl or ethyl.

4. N-hydroxy-1,2-dihydro-2-oxo-5-(4-pyridinyl)-nicotinimidamide or pharmaceutically-acceptable acid-addition salt thereof.

5. A cardiotonic composition for increasing cardiac contractility, said composition comprising a pharmaceutically-acceptable inert carrier and, as the active component thereof, a cardiotonically-effective amount of N-hydroxy-1-$R_1$-1,2-dihydro-2-oxo-5-PY-6-R-nicotinimidamide or pharmaceutically-acceptable acid-addition salt thereof, where R is hydrogen or lower-alkyl, $R_1$ is hydrogen, lower-alkyl or lower-hydroxyalkyl, and PY is 4- or 3-pyridinyl or 4- or 3-pyridinyl having one or two lower-alkyl substituents.

6. A composition according to claim 5 where PY is 4- or 3-pyridinyl, $R_1$ is hydrogen and R is hydrogen, methyl or ethyl.

7. The method for increasing cardiac contractility in a patient requiring such treatment which comprises administering to such patient a composition comprising a pharmaceutically-acceptable carrier and, as the active component thereof, a cardiotonically-effective amount of N-hydroxy-1-$R_1$-1,2-dihydro-2-oxo-5-PY-6-R-nicotinimidamide or pharmaceutically-acceptable acid-addition salt thereof, where R is hydrogen or lower-alkyl, $R_1$ is hydrogen, lower-alkyl or lower-hydroxyalkyl, and PY is 4- or 3-pyridinyl or 4- or 3-pyridinyl having one or two lower-alkyl substituents.

8. The method according to claim 7 where PY is 4- or 3-pyridinyl, $R_1$ is hydrogen and R is hydrogen, methyl or ethyl.

* * * * *